(12) United States Patent
Gross et al.

(10) Patent No.: US 8,755,893 B2
(45) Date of Patent: Jun. 17, 2014

(54) TIBIAL NERVE STIMULATION

(75) Inventors: Yossi Gross, Moshav Mazor (IL); Noam Kinrot, Nesher (IL); Gur Oron, Tel Aviv (IL); Shlomo Ronen, Raanana (IL); Ali Stern-Cohen, Moshav Beit-Yehoshua (IL); Danny Neeman, Ramat Hasharon (IL)

(73) Assignee: Bluewind Medical Ltd., Herzliya (IL)

( * ) Notice: Subject to any disclaimer, the term of this patent is extended or adjusted under 35 U.S.C. 154(b) by 0 days.

(21) Appl. No.: 13/528,433

(22) Filed: Jun. 20, 2012

(65) Prior Publication Data

US 2013/0066393 A1 Mar. 14, 2013

Related U.S. Application Data

(63) Continuation-in-part of application No. 12/796,102, filed on Jun. 8, 2010.

(51) Int. Cl.
*A61N 1/34* (2006.01)

(52) U.S. Cl.
USPC .......................................................... 607/46

(58) Field of Classification Search
USPC .............................................. 607/46, 48, 49
See application file for complete search history.

(56) References Cited

U.S. PATENT DOCUMENTS

| 3,411,507 | A | 4/1964 | Wingrove |
| 4,019,518 | A | 4/1977 | Maurer et al. |
| 4,338,945 | A | 7/1982 | Kosugi et al. |
| 4,392,496 | A | 7/1983 | Stanton |
| 4,535,785 | A | 8/1985 | Van Den Hornert et al. |
| 4,559,948 | A | 12/1985 | Liss et al. |
| 4,573,481 | A | 3/1986 | Bullara |
| 4,585,005 | A | 4/1986 | Lue et al. |
| 4,602,624 | A | 7/1986 | Naples et al. |
| 4,608,985 | A | 9/1986 | Crish et al. |
| 4,628,942 | A | 12/1986 | Sweeney et al. |
| 4,632,116 | A | 12/1986 | Rosen et al. |
| 4,649,936 | A | 3/1987 | Ungar et al. |
| 4,663,102 | A | 5/1987 | Brenman et al. |
| 4,739,764 | A | 4/1988 | Lue et al. |
| 4,867,164 | A | 9/1989 | Zabara |
| 4,926,865 | A | 5/1990 | Oman |
| 4,962,751 | A | 10/1990 | Krauter |
| 5,025,807 | A | 6/1991 | Zabara |

(Continued)

FOREIGN PATENT DOCUMENTS

EP 0 688 577 12/1995
WO 01/10375 2/2001

(Continued)

OTHER PUBLICATIONS

An Office Action dated Sep. 30, 2013, which issued during the prosecution of U.S. Appl. No. 12/796,102.

(Continued)

*Primary Examiner* — Alyssa M Alter
(74) *Attorney, Agent, or Firm* — Symbus Law Group, LLC; Clifford D. Hyra

(57) ABSTRACT

A method is provided, including identifying a subject as suffering from pain in a first limb of the subject. In response to the identifying, treatment of the pain in the first limb is facilitated by implanting electrodes in a limb of the subject that is contralateral to the first limb. Other embodiments are also described.

36 Claims, 6 Drawing Sheets

(56) References Cited

U.S. PATENT DOCUMENTS

| | | |
|---|---|---|
| 5,069,680 A | 12/1991 | Grandjean |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker, Jr. |
| 5,215,086 A | 6/1993 | Terry, Jr. et al. |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz |
| 5,335,657 A | 8/1994 | Terry, Jr. et al. |
| 5,423,872 A | 6/1995 | Cigaina |
| 5,439,938 A | 8/1995 | Snyder et al. |
| 5,454,840 A | 10/1995 | Krakovsky et al. |
| 5,505,201 A | 4/1996 | Grill, Jr. et al. |
| 5,540,730 A | 7/1996 | Terry, Jr. et al. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke et al. |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen et al. |
| 5,700,282 A | 12/1997 | Zabara |
| 5,707,400 A | 1/1998 | Terry, Jr. et al. |
| 5,711,316 A | 1/1998 | Elsberry et al. |
| 5,716,385 A | 2/1998 | Mittal et al. |
| 5,755,750 A | 5/1998 | Petruska et al. |
| 5,776,171 A | 7/1998 | Peckham et al. |
| 5,814,089 A | 9/1998 | Stokes et al. |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 5,944,680 A | 8/1999 | Christopherson et al. |
| 5,954,758 A | 9/1999 | Peckham et al. |
| 6,026,326 A | 2/2000 | Bardy |
| 6,026,328 A | 2/2000 | Peckham et al. |
| 6,058,331 A | 5/2000 | King |
| 6,066,163 A | 5/2000 | John |
| 6,083,249 A | 7/2000 | Familoni |
| 6,086,525 A | 7/2000 | Davey et al. |
| 6,091,977 A | 7/2000 | Tarjan et al. |
| 6,091,992 A | 7/2000 | Bourgeois et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,169,924 B1 | 1/2001 | Meloy et al. |
| 6,205,359 B1 | 3/2001 | Boveja |
| 6,212,435 B1 | 4/2001 | Lattner et al. |
| 6,230,061 B1 | 5/2001 | Hartung |
| 6,240,316 B1 | 5/2001 | Richmond et al. |
| 6,266,564 B1 | 7/2001 | Hill et al. |
| 6,272,383 B1 | 8/2001 | Grey et al. |
| 6,292,703 B1 | 9/2001 | Meier et al. |
| 6,319,241 B1 | 11/2001 | King et al. |
| 6,332,089 B1 | 12/2001 | Acker et al. |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,405,079 B1 | 6/2002 | Ansarinia |
| 6,449,507 B1 | 9/2002 | Hill et al. |
| 6,463,328 B1 | 10/2002 | John |
| 6,473,644 B1 | 10/2002 | Terry, Jr. et al. |
| 6,600,954 B2 | 7/2003 | Cohen et al. |
| 6,600,956 B2 | 7/2003 | Maschino et al. |
| 6,610,713 B2 | 8/2003 | Tracey |
| 6,618,627 B2 | 9/2003 | Lattner et al. |
| 6,641,542 B2 | 11/2003 | Cho et al. |
| 6,735,474 B1 | 5/2004 | Loeb et al. |
| 6,770,022 B2 | 8/2004 | Mechlenburg et al. |
| 6,829,508 B2 | 12/2004 | Schulman et al. |
| 6,839,594 B2 | 1/2005 | Cohen et al. |
| 6,892,098 B2 | 5/2005 | Ayal et al. |
| 6,909,917 B2 | 6/2005 | Woods et al. |
| 7,025,730 B2 | 4/2006 | Cho et al. |
| 7,027,860 B2 | 4/2006 | Bruninga et al. |
| 7,177,698 B2 | 2/2007 | Klosterman et al. |
| 7,228,178 B2 | 6/2007 | Carroll et al. |
| 7,277,749 B2 | 10/2007 | Gordon et al. |
| 7,324,852 B2 | 1/2008 | Barolat et al. |
| 7,324,853 B2 | 1/2008 | Ayal et al. |
| 7,536,226 B2 | 5/2009 | Williams et al. |
| 7,628,750 B2 | 12/2009 | Cohen et al. |
| 7,630,771 B2 | 12/2009 | Cauller |
| 7,660,632 B2 | 2/2010 | Kirby et al. |
| 7,680,538 B2 | 3/2010 | Durand et al. |
| 7,797,050 B2 | 9/2010 | Libbus et al. |
| 7,848,818 B2 | 12/2010 | Barolat et al. |
| 7,917,226 B2 | 3/2011 | Nghiem et al. |
| 7,974,706 B2 | 7/2011 | Moffitt et al. |
| 7,996,089 B2 | 8/2011 | Haugland et al. |
| 7,996,092 B2 | 8/2011 | Mrva et al. |
| 8,019,443 B2 | 9/2011 | Schleicher et al. |
| 8,131,377 B2 | 3/2012 | Shi et al. |
| 8,185,207 B2 | 5/2012 | Molnar et al. |
| 2002/0099419 A1 | 7/2002 | Cohen et al. |
| 2003/0040774 A1 | 2/2003 | Terry, Jr. et al. |
| 2003/0100933 A1 | 5/2003 | Ayal et al. |
| 2003/0176898 A1 | 9/2003 | Gross et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1* | 4/2004 | Firlik et al. .................... 607/48 |
| 2004/0254624 A1 | 12/2004 | Johnson |
| 2005/0143789 A1 | 6/2005 | Whitehurst et al. |
| 2005/0165457 A1 | 7/2005 | Benser et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0067000 A1 | 3/2007 | Strother et al. |
| 2007/0173893 A1 | 7/2007 | Pitts |
| 2008/0027513 A1 | 1/2008 | Carbunaru |
| 2008/0039915 A1 | 2/2008 | van den Biggelaar et al. |
| 2008/0103572 A1 | 5/2008 | Gerber |
| 2009/0012590 A1 | 1/2009 | Inman et al. |
| 2009/0048642 A1 | 2/2009 | Goroszeniuk |
| 2009/0281594 A1 | 11/2009 | King et al. |
| 2010/0121405 A1 | 5/2010 | Ternes et al. |
| 2010/0125310 A1 | 5/2010 | Wilson et al. |
| 2010/0198298 A1 | 8/2010 | Glukhovsky et al. |
| 2010/0241195 A1 | 9/2010 | Meadows et al. |
| 2010/0312320 A1 | 12/2010 | Faltys et al. |
| 2011/0046696 A1 | 2/2011 | Barolat et al. |
| 2011/0093036 A1 | 4/2011 | Mashiach |
| 2011/0137365 A1 | 6/2011 | Ben-Ezra et al. |
| 2011/0152965 A1 | 6/2011 | Mashiach et al. |
| 2011/0160798 A1 | 6/2011 | Ackermann et al. |
| 2011/0208271 A1 | 8/2011 | Dobak |
| 2011/0224744 A1 | 9/2011 | Moffitt et al. |
| 2011/0282412 A1 | 11/2011 | Glukhovsky et al. |
| 2011/0301670 A1 | 12/2011 | Gross et al. |
| 2012/0041511 A1 | 2/2012 | Lee |
| 2012/0065701 A1 | 3/2012 | Cauller |
| 2012/0083857 A1 | 4/2012 | Bradley et al. |
| 2012/0123498 A1 | 5/2012 | Gross |
| 2012/0130448 A1 | 5/2012 | Woods et al. |
| 2012/0130463 A1 | 5/2012 | Ben-David et al. |

(56) References Cited

U.S. PATENT DOCUMENTS

FOREIGN PATENT DOCUMENTS

| WO | 01/10432 | 2/2001 |
|---|---|---|
| WO | 01/26729 | 4/2001 |
| WO | 2004/064729 | 8/2004 |
| WO | 2011/154937 | 12/2011 |

OTHER PUBLICATIONS

C. de Balthasar, G. Cosendai, M. Hansen, D. Canfield, L. Chu, R. Davis, and J. Schulman, "Attachment of leads to RF-BION® microstimulators." Jul. 2005.
D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501-510.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration Physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023-2029.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662-1668.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643-652.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177-209.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.

An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/2006/03/patents_galore.html (Downloaded Jan. 2012).
Chris Seper, "Neuros Medical Launches to Develop New Device to Block Amputee, Chronic Pain", Mar. 16, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. and Psych. 1980, 43, 713-718.
Jobges et al., Vibratory proprioceptive stimulation affects Parkinsonian tremor. Parkinsonism & Related Disorders, 8(3), 171-176, Jan. 2002.
R.J. Mones, A.H. Weiss, The response of the tremor of patients with Parkinsonism to peripheral nerve stimulation. J. Neurol. Neurosurg. Psychiat. 1969, 32. 512-518.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
B.S. Russman, MD., Cerebral Palsy, Current Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/005069.
G.G. Naples et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).

(56) References Cited

OTHER PUBLICATIONS

Fitzpatrick et al., in "A nerve cuff design for the selective activation and blocking of myelinated nerve fibers," Ann. Conf. of the IEEE Eng. in Medicine and Biology Soc, 13(2), 906 (1991).

Rijkhoff NJ et al., "Orderly recruitment of motoneurons in an acute rabbit model," Ann. Conf. of the IEEE Eng., Medicine and Biology Soc., 20(5):2564 (1998).

Van den Honert C et al., "A technique for collision block of peripheral nerve: Frequency dependence," MP-12, IEEE Trans. Biomed. Eng. 28:379-382 (1981).

Baratta R et al., "Orderly stimulation of skeletal muscle motor units with tripolar nerve cuff electrode," IEEE Transactions on Biomedical Engineering, 36(8):836-43 (1989).

Van den Honert C et al., "Generation of unidirectionally propagated action potentials in a peripheral nerve by brief stimuli," Science, 206:1311-1312 (1979).

M. Devor, "Pain Networks", Handbook of Brand Theory and Neural Networks, ED M.A. Arbib MIT Press pp. 698-702, 1998.

Epilepsy center. http://www.bcm.tmc.edu/neural/struct/epilep/epilpsy_vagus.html. May 31, 2011 (2 Versions).

J.F. Cortese, "Vagus Nerve Stimulation for Control of Intractable Epileptic Seizures", May 31, 2001.

Evetovich T.K. et al., Gender comparisons of the mechanomyographic responses to minimal concentric and eccentric isokinetic muscle actions, Medicine & Science in Sports & Exercise, 1998 pp. 1697-1702. Abstract.

Dean, J. et al., "Motor Pattern Generation", Handbook of Brain Theory and Neural Networks, pp. 596-701.

* cited by examiner

FIG. 3A
FIG. 3B
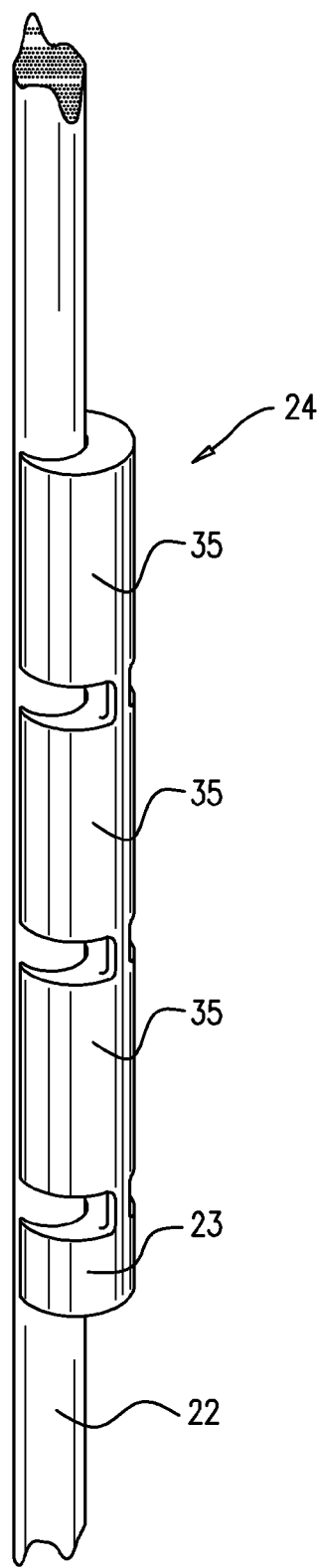
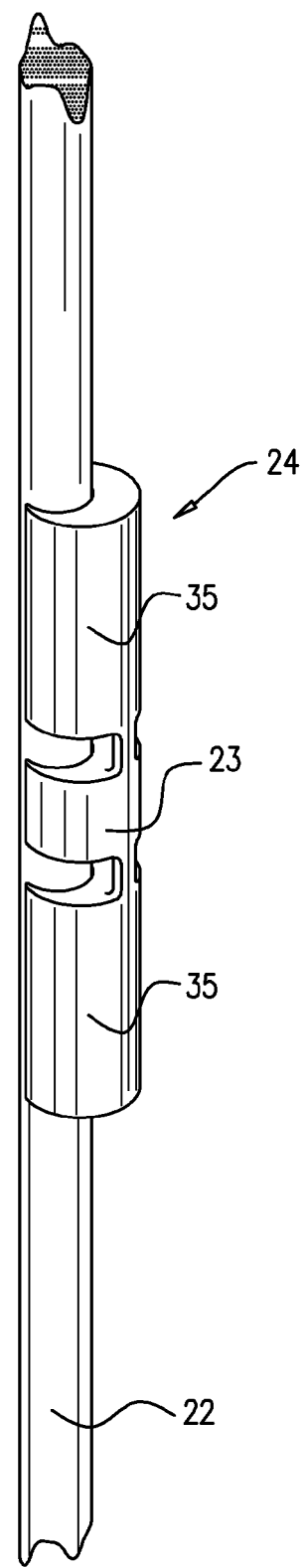

TIBIAL NERVE STIMULATION

CROSS-REFERENCES TO RELATED APPLICATIONS

The present application is a continuation-in-part of U.S. Ser. No. 12/796,102 (which published as US 2011/0301670 to Gross), filed Jun. 8, 2010, which is incorporated herein by reference.

FIELD OF EMBODIMENTS OF THE INVENTION

Some applications of the present invention generally relate to medical apparatus. Specifically, some applications of the present invention relate to stimulation of the tibial nerve.

BACKGROUND

Polyneuropathy is a disease of the peripheral nerves. Typically, patients suffering from polyneuropathy experience chronic pain. In many cases polyneuropathy is a symptom of diabetes mellitus.

The tibial nerve is a branch of the sciatic nerve that passes alongside the tibia and into the foot. At the ankle, the tibial nerve is relatively close to the surface of the skin. In percutaneous tibial nerve stimulation, a percutaneous electrode is inserted into the subject's ankle, and the tibial nerve is stimulated, for example, in order to treat pelvic pain and/or incontinence.

U.S. Pat. No. 6,735,474 to Loeb describes a method and system for treatment of incontinence and/or pelvic pain including the injection or laparoscopic implantation of one or more battery- or radiofrequency-powered microstimulators beneath the skin of the perineum and/or adjacent the tibial nerve. The devices are described as being programmed using radio-frequency control via an external controller that can be used by a physician to produce patterns of output stimulation pulses judged to be efficacious by appropriate clinical testing to diminish symptoms. The stimulation program is described as being retained in the microstimulator device or external controller and as being transmitted when commanded to start and stop by a signal from the patient or caregiver. The system and method are described as reducing the incidence of unintentional episodes of bladder emptying by stimulating nerve pathways that diminish involuntary bladder contractions, improving closure of the bladder outlet, and/or improving the long-term health of the urinary system by increasing bladder capacity and period between emptying. The incidence of fecal incontinence is described as being similarly reduced or eliminated. Furthermore, the system and method are described as reducing or eliminating the incidence of pelvic pain by chronically stimulating nerve pathways that derive from the sacral roots using a miniature implantable neurostimulator that can be implanted with a minimal surgical procedure. The system and method are described as allowing a patient to be taught to receive one or more patterns of neural stimulation that can be prescribed by a physician and administered without continuous oversight by a clinical practitioner.

Neuros Medical (Ohio, USA) manufactures a system that is described as delivering high-frequency stimulation to sensory nerves in the peripheral nervous system to block chronic pain. The system consists of an electrode (also known as a lead) placed around a peripheral nerve and powered by a pace-maker size generator that is implanted into the chest cavity, abdomen, or lower leg. In a press release, dated Mar. 17, 2009 it was stated that the generator operates in a much higher frequency range than conventional neurostimulation devices, and, therefore, the technology is able to stop nerve activity to block pain completely, as opposed to simply masking the pain signal.

Uroplasty Inc. (Minnesota, USA) manufactures the Urgent® PC Neuromodulation System, which is described as using percutaneous tibial nerve stimulation (PINS) for treating urinary urgency, urinary frequency, and urge incontinence.

The following references may be of interest:
U.S. Pat. No. 7,536,226 to Williams
U.S. Pat. No. 6,829,508 to Schulman
U.S. Pat. No. 6,272,383 to Grey
US 2008/0039915 to Van Den Biggelaar
US 2006/0271137 to Stanton-Hicks
US 2006/0155345 to Williams
US 2005/0143789 to Whitehurst
US 2004/0254624 to Johnson "Is electrical stimulation effective in reducing neuropathic pain in patients with diabetes?" by Armstrong, J Foot Ankle Surg. 1997 July-August; 36(4):260-3

"Responses to Median and Tibial Nerve Stimulation in Patients with Chronic Neuropathic Pain," by Theuvenet, Brain Topography, Volume 11, Number 4, 1999, pp. 305-313 (9)

SUMMARY OF EMBODIMENTS

For some applications of the present invention, a subject is identified as suffering from polyneuropathy. Electrodes are disposed on a housing that is at least partially flexible. The electrodes are placed in contact with the subject's tibial nerve. The polyneuropathy is treated by driving a current into the tibial nerve, via the electrodes. Typically, the housing is such that it maintains contact between the electrodes and the tibial nerve. A control unit that is typically disposed outside of the subject's body drives the electrodes. For example, the control unit may be coupled to a sock that is worn by the subject.

There is therefore provided, in accordance with an application of the present invention, a method, including:
identifying a subject as suffering from pain in a first limb of the subject; and
in response to the identifying, facilitating treating of the pain in the first limb by implanting electrodes in a limb of the subject that is contralateral to the first limb.

In an application, identifying the subject as suffering from pain in the first limb, includes identifying a subject as suffering from pain in a limb that has been damaged by trauma.

In an application, identifying the subject as suffering from pain in the first limb, includes identifying a subject as suffering from phantom pain in a limb that has been amputated.

In an application, identifying the subject as suffering from pain in the first limb, includes identifying a subject as suffering from pain in a limb that is contralateral to a limb that has been amputated, and implanting electrodes in the contralateral limb includes implanting electrodes in a stump of the limb that has been amputated.

In an application, identifying includes identifying the subject as suffering from neuropathic pain in the first limb.

In an application, identifying the subject as suffering from pain in the first limb, includes identifying a subject as suffering from pain in a limb that has been damaged by disease.

In an application, identifying the subject includes identifying a subject as suffering from pain in a limb that has been damaged by diabetes.

In an application, the method further includes driving the electrodes to apply a current to the contralateral limb.

In an application, driving the electrodes includes driving the electrodes from outside a body of the subject.

In an application, driving the electrodes from outside the body of the subject includes driving the electrodes using a control unit that is coupled to an element that is coupled to the contralateral limb.

In an application, driving the electrodes to apply the current includes driving the electrodes to apply a current having a frequency of 10 Hz to 100 Hz.

In an application, driving the electrodes to apply the current includes driving the electrodes to apply a current having a frequency of 20 Hz to 100 Hz.

In an application, driving the electrodes to apply the current includes driving the electrodes to apply a current having a frequency of 20 Hz to 40 Hz.

In an application, driving the electrodes to apply the current includes driving the electrodes to apply a current having a frequency of 40 Hz to 60 Hz.

In an application, driving the electrodes to apply the current includes driving the electrodes to apply the current for a therapy period having a duration of between two minutes and ten minutes.

In an application, driving the electrodes to apply the current for the therapy period includes driving the electrodes to apply the current during 2-8 therapy periods per day.

In an application, driving the electrodes to apply the current for the therapy period includes driving the electrodes to apply the current during 2-8 therapy periods per week.

In an application, driving the electrodes to apply the current includes driving the electrodes to apply a current having an amplitude of up to 10 mA.

In an application, driving the electrodes to apply the current includes driving the electrodes to apply a current having an amplitude of between 0.2 mA and 8 mA.

In an application, driving the electrodes to apply the current includes driving the electrodes to apply a current having an amplitude of between 0.5 mA and 4 mA.

In an application, the method further includes detecting a myographic signal of the subject, and driving the electrodes includes driving the electrodes responsively to the myographic signal.

In an application, implanting the electrodes in the contralateral limb includes placing the electrodes within 1 mm of a tibial nerve of the contralateral limb.

In an application, placing the electrodes includes placing the electrodes within 0.5 mm of the tibial nerve of the contralateral limb.

In an application, placing the electrodes includes placing the electrodes within 0.3 mm of the tibial nerve of the contralateral limb.

In an application, placing the electrodes includes placing the electrodes in contact with the tibial nerve of the contralateral limb.

In an application, placing the electrodes includes inserting the electrodes into the tibial nerve.

In an application, inserting the electrodes into the tibial nerve includes expanding a spring, the electrodes being coupled to the spring.

In an application, the electrodes are disposed on a housing, and implanting the electrodes includes implanting the housing on which the electrodes are disposed.

In an application, implanting the electrodes includes, when the electrodes are driven to drive the current into the tibial nerve, reducing a current path from the electrodes away from the tibial nerve, using the housing, by placing the electrodes within 1 mm of the tibial nerve, between the nerve and the housing.

In an application, implanting the housing includes implanting a housing that is at least partially flexible.

In an application, the housing includes flexible and rigid portions thereof, the portions being articulatably coupled to each other, and implanting the electrodes includes implanting the housing that includes the flexible and the rigid portions thereof.

In an application, implanting the electrodes includes placing the electrodes within 1 mm of a tibial nerve of the contralateral limb.

In an application, placing the electrodes within 1 mm of the tibial nerve of the subject includes injecting the housing into an ankle of the subject.

In an application, placing the electrodes within 1 mm of the tibial nerve of the subject includes coupling the housing to the tibial nerve via one or more coupling elements that are coupled to the housing.

In an application, coupling the housing to the tibial nerve via the one or more coupling elements includes coupling the housing to the tibial nerve via one or more spiral coupling elements.

In an application, placing the electrodes within 1 mm of the tibial nerve of the subject includes inserting the electrodes into the tibial nerve.

In an application, inserting the electrodes into the tibial nerve includes positioning the electrodes adjacent to the tibial nerve by moving the housing alongside the tibial nerve in a first direction, and, subsequently, inserting the electrodes into the tibial nerve by moving the housing in a second direction, the second direction being opposite to the first direction.

There is further provided, in accordance with an application of the present invention, apparatus for treating polyneuropathy of a subject, including:

one or more electrodes configured to be placed in contact with a portion of the subject's body within 1 mm of a tibial nerve of the subject;

a housing that is at least partially flexible configured to support the electrodes and to maintain contact between the electrodes and the portion by bending; and a control unit configured to be placed outside a body of the subject, and to drive the electrodes to treat the polyneuropathy by driving a current into the tibial nerve.

The present invention will be more fully understood from the following detailed description of embodiments thereof, taken together with the drawings, in which:

BRIEF DESCRIPTION OF THE DRAWINGS

FIGS. 3A-B are schematic illustrations of housings having rigid and flexible portions thereof, in accordance with some applications of the present invention;

DETAILED DESCRIPTION OF EMBODIMENTS

Figure 1:
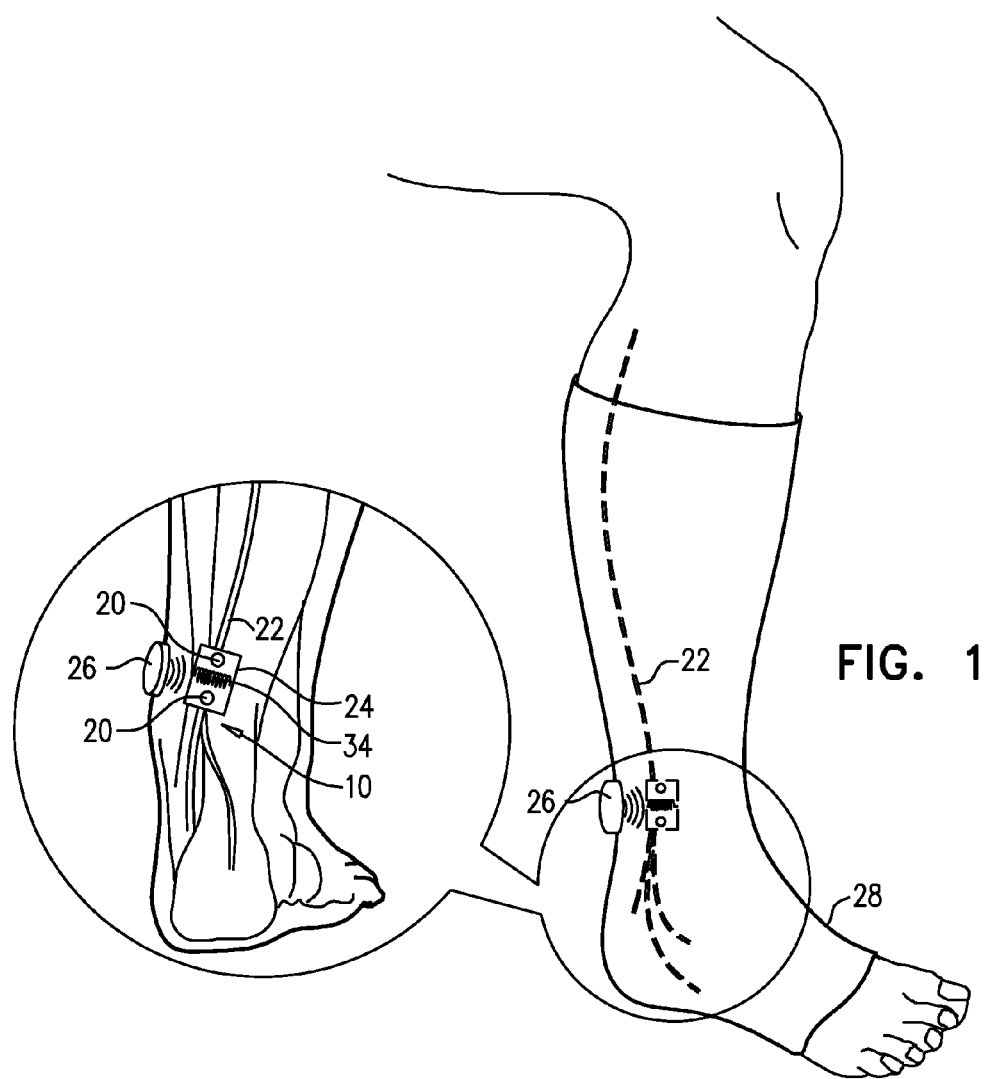
FIG. 1 is a schematic illustration of electrodes for stimulating the tibial nerve, in accordance with some applications of the present invention.

Reference is now made to FIG. 1, which is a schematic illustration of an implantable element 10 that includes electrodes 20 for stimulating a subject's tibial nerve 22, in accordance with some applications of the present invention. The electrodes are typically implanted in contact with the tibial nerve (e.g., by inserting the electrodes into the nerve, and/or by placing a housing 24 in contact with the nerve, the electrodes being disposed inside the housing). For some applications, the electrodes are implanted within 0.5 mm of the tibial nerve, e.g., within 0.3 mm of the tibial nerve. Alternatively, the electrodes are implanted at a distance of more than 0.5 mm, and/or less than 1 mm from the tibial nerve, e.g., within 0.5 mm to 1 mm from the tibial nerve. The electrodes are typically implanted on or near the tibial nerve, at a position in the vicinity of the subject's ankle. At this location, the tibial nerve is relatively close to the surface of the skin. Thus, in order to implant the electrodes at this location, it is typically not required to penetrate deeply into the subject's tissue. Typically, the electrodes are implanted in order to treat a subject who is identified as suffering from polyneuropathy.

Typically, electrodes 20 are disposed on a housing 24, at least a portion of which is flexible (e.g., a flexible silicone housing). The flexibility of the housing maintains contact between electrodes 20 and tibial nerve 22, even though the region of the subject's body in the vicinity of the implantation site undergoes significant motion. For some applications, the housing is an elongated silicone housing. Two electrodes are disposed inside the housing, there being gaps in the housing to provide contact of the electrodes with the tibial nerve. For some applications, a portion of the housing is not flexible, although most of the housing is flexible.

Typically, the disposition of electrodes 20 with respect to housing 24, and/or the shape of the housing is such that the current path of current from the electrodes, away from the tibial nerve is reduced. For example, the electrodes may be disposed on an inner surface of a housing that is placed around the tibial nerve, such that the housing directs the current flow toward the tibial nerve and reduces the current flow away from the tibial nerve.

For some applications, the housing is shaped as a cuff. For some applications, coupling elements (for example, a flexible hook (e.g., a silicone hook)), extend from housing 24 and are configured to couple the housing to the nerve, for example, in accordance with the techniques described hereinbelow. Alternatively or additionally, staples, a biological adhesive, and/or sutures are applied to the tibial nerve, and/or to tissue in the vicinity of the tibial nerve, in order to couple the housing to the nerve. Further alternatively or additionally, a mesh (e.g., a Dacron mesh) is disposed on an outer surface of the housing. The mesh causes fibrosis in the vicinity of the housing, thereby stabilizing the housing.

For some applications, electrodes 20 are disposed on a flexible coil that is placed around tibial nerve 22. The flexibility of the coil is typically such that the coil maintains contact between electrodes 20 and tibial nerve 22, even though the region of the subject's body in the vicinity of the implantation site undergoes significant motion. For some applications, the coil is placed around the tibial nerve in a minimally-invasive surgical procedure.

Electrodes 20 are actuated to drive a current into the tibial nerve by an external controller 26, which is external to the subject's body. For some applications, as shown in FIG. 1, the controller is coupled to a sock that is worn by the subject. Alternatively, the controller is placed in the vicinity of the electrodes, and outside the subject's body by alternative means, for example, by strapping external controller 26 to the subject's ankle, and/or by applying a patch to the subject's ankle, controller 26 being coupled to the patch. Further alternatively, controller 26 is coupled to housing 24, and is implanted in the vicinity of the tibial nerve.

Figure 2:
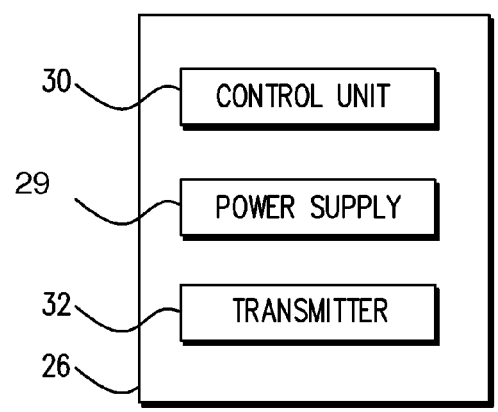
FIG. 2 is a block diagram of an external controller, in accordance with some applications of the present invention.

Reference is now made to FIG. 2, which is a block diagram of external controller 26, in accordance with some applications of the present invention. The external controller typically includes a power supply 29, a control unit 30, and a transmitter 32. In a typical application, the control unit wirelessly transmits a signal to implantable element 10, via the transmitter. An antenna 34 (shown in FIG. 1) of implantable element 10 receives the signal and relays the signal to the electrodes. The signal drives the electrodes to drive a current into the tibial nerve. The control unit typically comprises at least one power coupling element, a frequency down-converter, and at least one rectifier. For some applications, the control unit is configured to receive a signal, e.g., a myographic signal, and to actuate the electrodes responsively thereto.

The current that is driven into the tibial nerve typically has a frequency of more than 10 Hz, e.g., more than 20 Hz, and/or less than 100 Hz (e.g., 10-100 Hz, e.g., 20-100 Hz, e.g., 20-40 Hz). For example, the frequency may be more than 30 Hz, and/or less than 80 Hz (e.g., 30-80 Hz), or more than 40 Hz, and/or less than 60 Hz (e.g., 40-60 Hz). The current typically has an amplitude of more than 0.2 mA, and/or less than 8 mA (e.g., 0.2-8 mA). For example, the amplitude may be more than 0.5 mA, and/or less than 4 mA (e.g., 0.5-4 mA). For some applications, for example, if the electrodes cannot be placed in close proximity to the tibial nerve, an amplitude of up to 10 mA is used.

For some applications, the location of the posterior tibial nerve is determined in accordance with the following procedure, and implantable element 10 is implanted based on the determined location. The skin of the subject is stimulated (typically electrically) at a distal site, e.g., on the sole of the foot. Nerve conduction signals along the tibial nerve that result from the stimulation are detected, in order to determine the location of the tibial nerve. Alternatively or additionally, sites in the subject's ankle are stimulated. In order to localize the tibial nerve, the response of a foot muscle (e.g., the abductor hallucis) of the subject to the stimulation at respective sites is recorded, typically, in accordance with nerve localization techniques that are known in the art.

Reference is now made to FIGS. 3A-B, which are schematic illustrations of housing 24 having rigid portions 23 and flexible portions 35 thereof. For some applications, as shown, the housing includes a plurality of portions, which are coupled to each other articulatably (i.e., in a manner that facilitates movement of the portions with respect to each other), typically via joints (as shown).

Typically, electronic control components (e.g., antenna 34, and/or another control component for receiving a signal from control unit 26) are disposed within a rigid seal (such as glass or metal) in one or more rigid portions. The electrodes are disposed on the flexible portions, such that contact between the electrodes and the tibial nerve is maintained due to the flexibility of the portion. For some applications, the flexible portions are made of a polymer and/or silicone. For some applications, the flexibility of the flexible portions is less than the flexibility provided by the joints, which couple the portions to each other. Typically, the flexible portions and/or the rigid portions are coupled to the tibial nerve in accordance with the techniques described herein.

For some applications, a single rigid portion is disposed at one end of the housing, as shown in FIG. 3A. Alternatively, a single rigid portion is disposed in a central region of the housing, as shown in FIG. 3B. Further alternatively, other combinations of flexible and rigid housing portions are used, as would be obvious to one skilled in the art, having read the specification of the present patent application.

Electrodes 20 are typically disposed on an inner surface of flexible portions of the housing. Alternatively, the electrodes are disposed at other positions on the housing. Typically, electrodes 20 are spaced at a distance of 8-10 mm from each other. Depending on the length of each of the flexible portions, a single electrode, or a plurality of electrodes are disposed on each of the flexible portions.

Figure 4A:
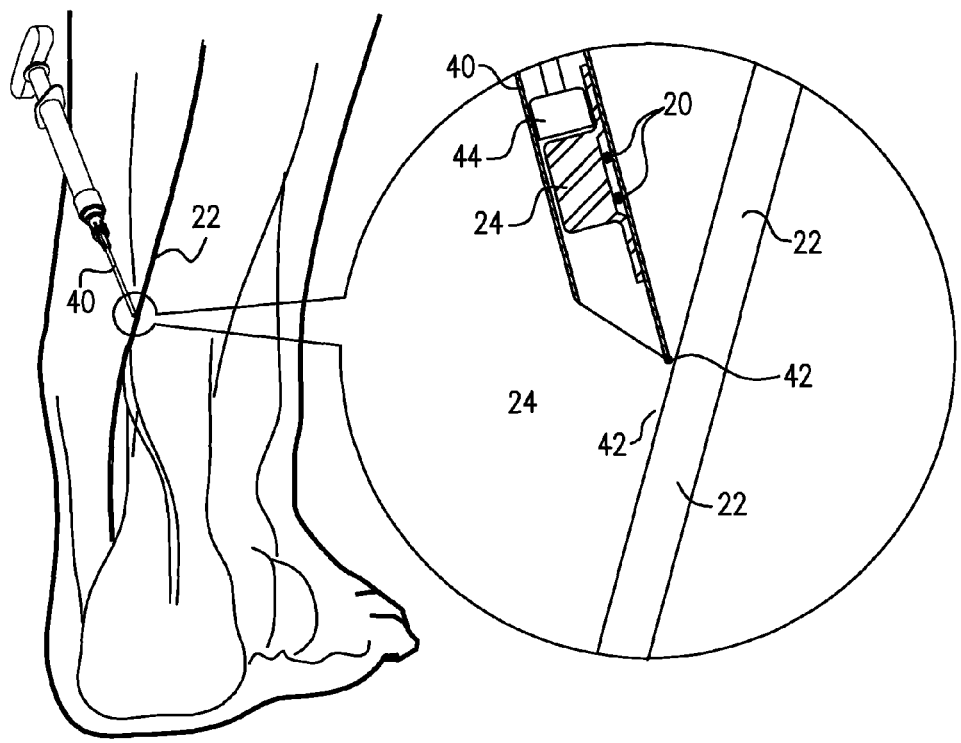
FIG. 4A is a schematic illustration of electrodes on a housing being injected into a subject's ankle to a vicinity of the tibial nerve, using an introducer, in accordance with some applications of the present invention.

Reference is now made to FIG. 4A, which is a schematic illustration of electrodes 20 on housing 24 being injected into the subject's ankle to a vicinity of tibial nerve 22, using an introducer 40, in accordance with some applications of the present invention. For some applications, at least one electrode 42 is disposed on the distal end of introducer 40 (as shown). Alternatively, at least one electrode 42 is disposed on the distal end of a dedicated electrode needle, the dedicated electrode needle being extendible from the distal end of introducer 40.

For some applications, electrodes 42 are stimulating electrodes. The electrodes are moved along the subject's tibial nerve and are used to stimulate the subject's tibial nerve. An implantation site for housing 24 is selected based upon the subject's response to the stimulation of the tibial nerve by electrodes 42, in accordance with the techniques described hereinabove. For some applications, a site of the tibial nerve is chosen as the implantation site, based upon the subject feeling pain relief when the stimulating electrodes stimulate the site.

Alternatively or additionally, electrodes 42 are sensing electrodes. The sensing electrodes are used to detect the location of the tibial nerve, and/or to determine a suitable implantation site for housing 24, by detecting action potentials. For example, the electrodes may detect action potentials generated in the tibial nerve in response to the subject's foot being electrically stimulated, in accordance with the techniques described hereinabove.

Figure 4B:
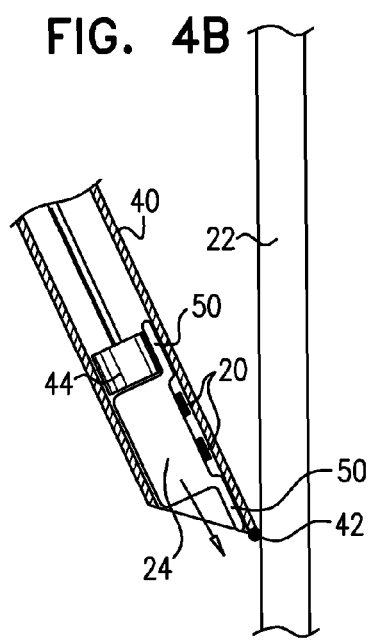
FIGS. 4B-D are schematic illustrations of respective steps of the housing being placed in the vicinity of the tibial nerve, in accordance with some applications of the present invention.
Figure 4C:
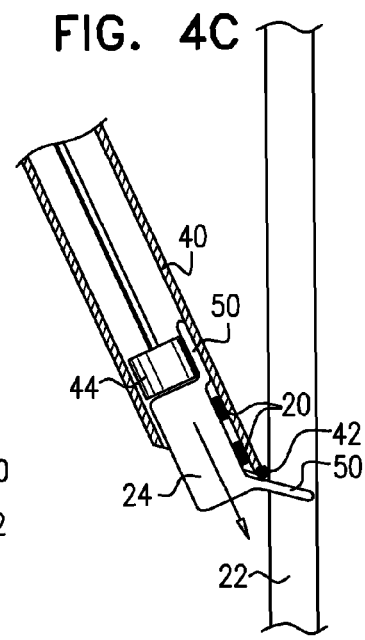
Figure 4D:
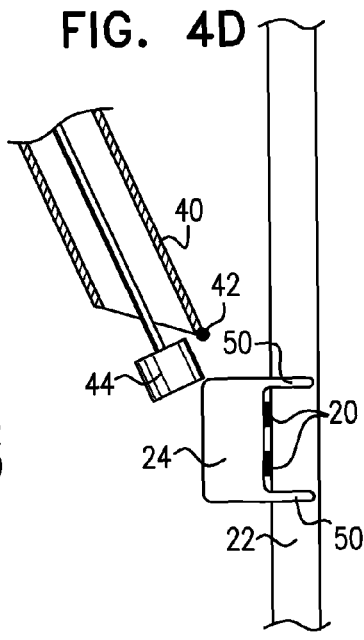

Reference is now made to FIGS. 4B-D, which are schematic illustrations of respective steps of housing 24 being injected to a vicinity of tibial nerve 22, in accordance with some applications of the present invention. For some applications, flexible coupling elements 50 are coupled to housing 24 and are disposed distally to the housing during injection of the housing into the subject's body, via introducer 40. For some applications, the coupling elements function as electrodes 20.

In a first step of the injection procedure, the distal end of introducer 40 is placed in the vicinity of tibial nerve 22, e.g., within 0.3 mm of the tibial nerve, such as within 0.5 mm (or within more than 0.5 mm, and/or less than 1 mm) of the tibial nerve. FIG. 4B shows the distal end of the introducer being placed in the vicinity of the tibial nerve. For some applications, the distal end of the introducer is positioned in response to stimulation and or sensing of electrodes 42, as described with reference to FIG. 4A.

Once the distal end of introducer 40 is suitably positioned, a pushing element 44 is used to push housing 24 distally, through introducer 40. Upon emerging from the distal end of the introducer, one or more distal coupling elements 50 curve outwards (FIG. 4C) and anchor themselves to tissue, for example, to tibial nerve 22 (FIG. 4C), or to tissue in the vicinity of the tibial nerve (e.g., within 0.3 mm of the tibial nerve, such as within 0.5 mm (or within more than 0.5 mm, and/or less than 1 mm) of the nerve).

Subsequent to the anchoring of distal coupling element 50 to the tissue, pushing element 44 continues to push housing 24 out of the distal end of introducer 40. When the proximal end of housing 24 emerges from the distal end of the introducer, proximal coupling element 50 couples the proximal end of the housing to the nerve, as shown in FIG. 4D.

Figure 4E:
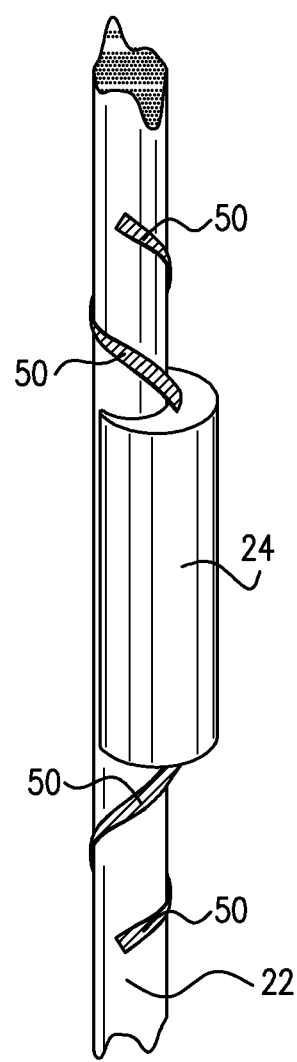
FIG. 4E is a schematic illustration of a housing having spiral coupling elements, in accordance with some applications of the present invention.

Reference is now made to FIG. 4E, which is a schematic illustration of housing 24 having spiral coupling elements 50, in accordance with some applications of the present invention. As shown, for some applications, the coupling elements are spirals, which couple housing 24 to the tibial nerve by curving around the tibial nerve. For some applications, the spiral coupling elements function as electrodes 20. Alternatively or additionally, electrodes 20 are disposed on the coupling elements and/or on housing 24.

Figure 5A:
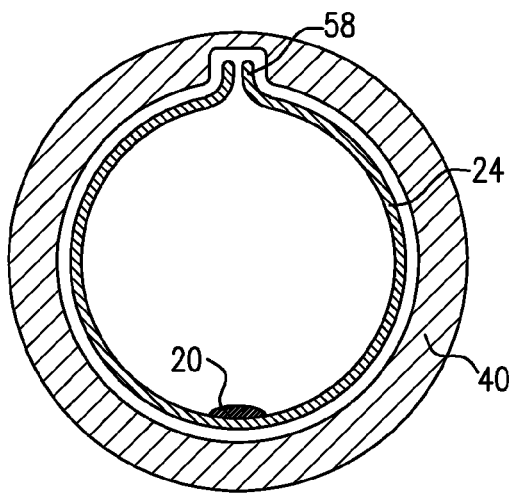
FIGS. 5A-B are schematic illustrations of a housing that is shaped to facilitate alignment of the housing with the tibial nerve, in accordance with some applications of the present invention.
Figure 5B:
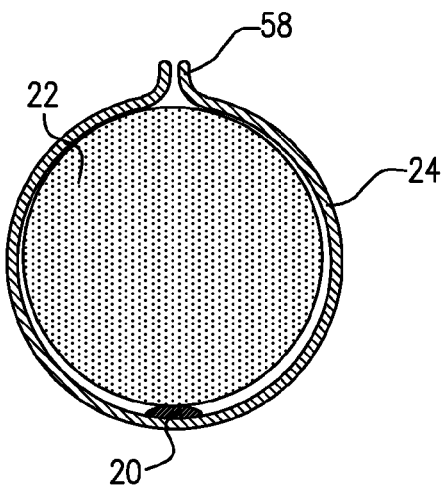

Reference is now made to FIGS. 5A-B, which are cross-sections of housing 24, shaped to facilitate alignment of the housing with the tibial nerve, in accordance with some applications of the present invention. FIG. 5A shows the housing during insertion of the housing into the subject's body, via introducer 40, and FIG. 5B shows the housing disposed on tibial nerve 22.

For some applications, a protrusion 58 protrudes from housing 24. Introducer 40 is shaped to define a lumen, a cross-section of which includes a groove that corresponds to the protrusion from the housing, as shown in FIG. 5A. Electrode 20 is coupled to the housing in a rotational position that is fixed with respect to the protrusion from the housing, for example, opposite the protrusion, as shown. Thus, during insertion of the housing into the subject's body and to the vicinity of the tibial nerve, the rotational location of the electrode with respect to the introducer may be controlled.

Typically, the introducer is oriented such that the electrode is placed in direct contact with the tibial nerve, as shown in FIG. 5B, or within 0.3 mm of the tibial nerve, such as within 0.5 mm (or within more than 0.5 mm, and/or less than 1 mm) of the nerve. Further typically, placing the electrode in direct contact with or within this distance of the tibial nerve reduces energy loss from the electrode, for example, relative to if the electrode were placed further from the tibial nerve. In addition, the shape of the injectable housing reduces the current path of current from the electrode, away from the tibial nerve.

Alternatively to the configuration of the apparatus shown in FIG. 5A, housing 24 is shaped to define a groove, and the introducer is shaped to define a lumen having a cross-section that includes a protrusion.

Figure 6A:
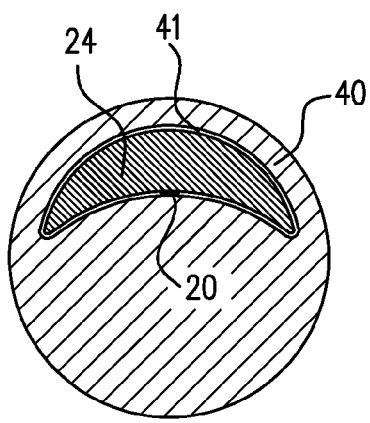
FIGS. 6A-B are schematic illustrations of a housing that is shaped to facilitate alignment of the housing with the tibial nerve, in accordance with some applications of the present invention.
Figure 6B:
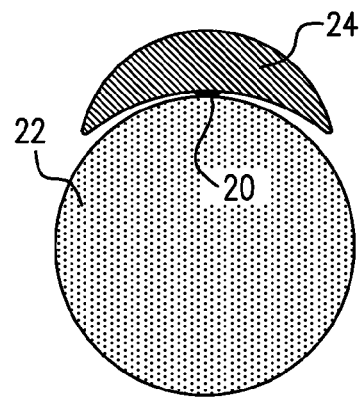

Reference is now made to FIGS. 6A-B, which are schematic illustrations of housing 24, shaped to facilitate alignment of the housing with tibial nerve 22, in accordance with some applications of the present invention. FIG. 6A shows the housing during insertion of the housing into the subject's body, via introducer 40, and FIG. 6B shows the housing disposed on tibial nerve 22.

For some applications, housing 24 has a non-circular cross-section. For example, the cross-section of the housing may be crescent shaped, as shown in FIGS. 6A-B. Introducer 40 is shaped to define a lumen 41 having a cross-section that corresponds to the shape of the cross-section of the housing, such that the housing can only be inserted through the lumen in a given rotational orientation. Electrode 20 is fixedly coupled to the housing. Thus, during insertion of the housing into the subject's body and to the vicinity of the tibial nerve, the rotational location of the electrode with respect to the introducer may be controlled. Typically, the introducer is oriented such that the electrode is placed in direct contact with the tibial nerve, as shown in FIG. 6B, or within 0.3 mm of the tibial nerve, such as within 0.5 mm (or within more than 0.5 mm, and/or less than 1 mm) of the nerve.

Figure 7A:
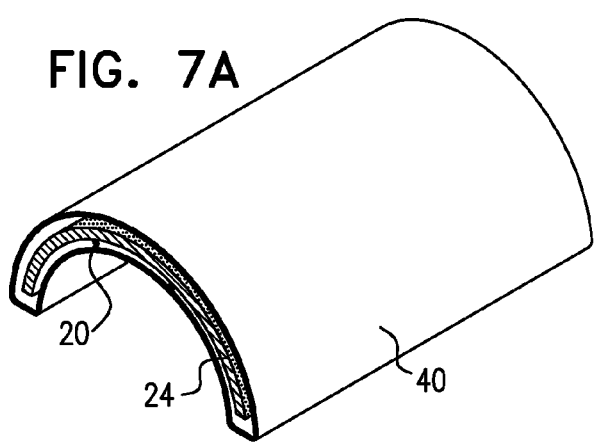
FIGS. 7A-C are schematic illustrations of a housing that undergoes a shape change, in accordance with some applications of the present invention.
Figure 7B:
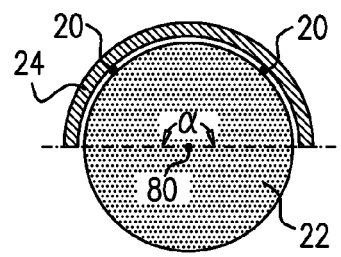
Figure 7C:
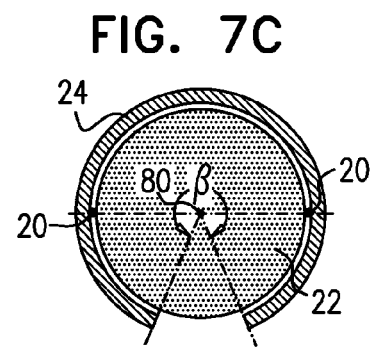

Reference is now made to FIGS. 7A-C, which are schematic illustrations of a housing 24 that undergoes a shape change, in accordance with some applications of the present invention. For some applications, housing 24 is placed on tibial nerve 22, while the housing has a first shape thereof. For example, FIG. 7A shows the housing in a first shape thereof inside introducer 40 (i.e., during insertion of the housing into the subject's body), and 7B shows the housing, in the first shape thereof, disposed on the tibial nerve. For some applications, while the housing is disposed around the tibial nerve in the first shape thereof, the housing defines an angle alpha around a longitudinal axis 80 of the tibial nerve of less than 180 degrees (as shown) or less, e.g., less than 90 degrees.

Typically, subsequent to the housing having been placed on or in the vicinity of the tibial nerve, the shape of the housing is changed to a second shape thereof. For example, the housing may comprise nitinol and/or another shape-change material, and the shape of the housing is changed by heating the housing. FIG. 7C shows the housing disposed around the tibial nerve in the second shape thereof. For some applications, while the housing is disposed around the tibial nerve in the second shape thereof, the housing defines an angle beta around longitudinal axis 80 of the tibial nerve of more than 180 degrees, e.g., 270 degrees or more.

Figure 8A:
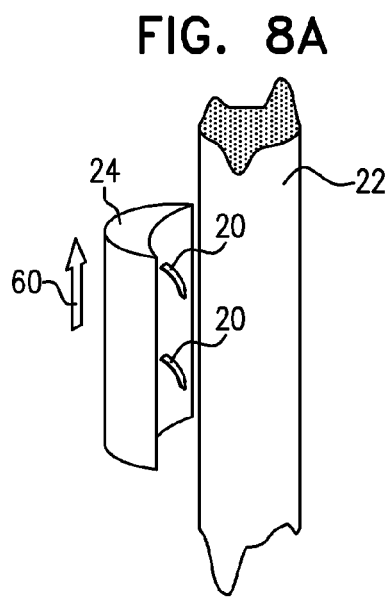
FIGS. 8A-B are schematic illustrations of electrodes being inserted into the tibial nerve, in accordance with some applications of the present invention.
Figure 8B:
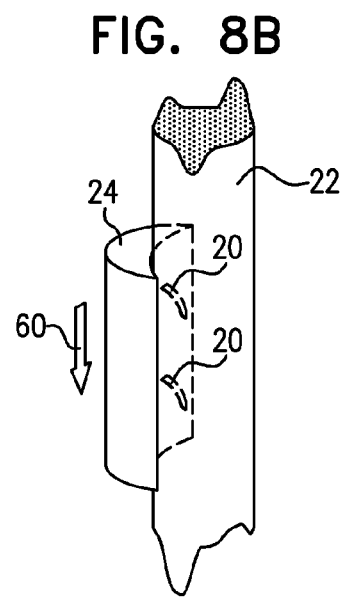

Reference is now made to FIGS. 8A-B, which are schematic illustrations of electrodes 20 that are configured to be inserted into the tibial nerve, in accordance with some applications of the present invention. Electrodes are disposed on housing 24, and are generally similar to electrodes 20 described hereinabove. During insertion of the electrodes to the vicinity of tibial nerve 22, housing 24 is advanced in the direction of arrow 60, such that even if the electrodes contact the tibial nerve, the electrodes slide past the tibial nerve, as shown in FIG. 8A. Subsequently, the housing is withdrawn in the direction of arrow 62. This causes electrodes 20 to become inserted into the tibial nerve, as shown in FIG. 8B.

Figure 9A:
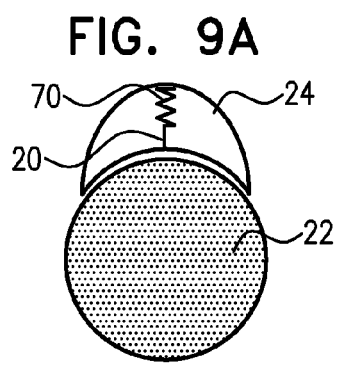
FIGS. 9A-B are schematic illustrations of electrodes being inserted into the tibial nerve, in accordance with some applications of the present invention.
Figure 9B:
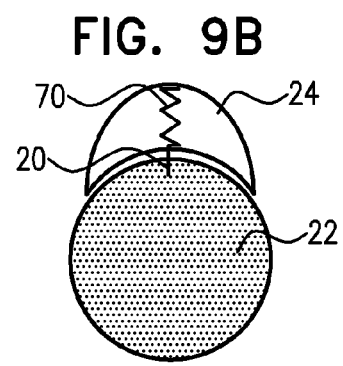

Reference is now made to FIGS. 9A-B, which are schematic illustration of electrodes 20 being inserted into tibial nerve 22, in accordance with some applications of the present invention. For some applications, electrodes 20 are needle electrodes. A spring 70 is disposed inside housing 24. Housing 24 is positioned adjacent to the tibial nerve while the spring is in a constricted configuration, as shown in FIG. 9A. When the housing is positioned at an implantation location of the housing, spring 70 is allowed to expand. Expansion of the spring pushes the needle electrodes into the tibial nerve.

For some applications, insertion of electrodes 20 into tibial nerve 22 in accordance with the techniques described with reference to FIGS. 8A-B and/or FIGS. 9A-B, anchors housing 24 to the tibial nerve. Alternatively or additionally, other techniques are used for anchoring the housing to the tibial nerve. For some applications, insertion of the electrodes into the tibial nerve maintains contact between the electrodes and the tibial nerve.

The inventors of the present application conducted an experiment in which EMG stimulating needle electrodes were inserted in close proximity to the tibial nerve of nine patients. In all of the patients, the electrode was placed in proximity to the tibial nerve on one side of the patient, and not in proximity to the tibial nerve of the other side of the patient. All of the patients suffered from a level of pain that was 2-9, based upon the following scale:

0-1: No pain
2-3: Mild pain
4-5: Discomforting—moderate pain
6-7: Distressing—severe pain
8-9: Intense—very severe pain
10: Unbearable pain Eight of the subjects were suffering from polyneuropathy, or neuropathic pain. One subject did not suffer from neuropathy, and may have been suffering from fibromyalgia. All patients were treated for 30 minute treatment sessions. Each treatment session was divided into five cycles of six minutes each, the cycles including five minutes of stimulation and a one minute pause. The patients were stimulated with a stimulating signal having an amplitude of 2-8 mA, and a frequency of 50 Hz.

All eight neuropathy patients, without exception, experienced marked alleviation of the neuropathic pain in the stimulated leg during stimulation. There was no beneficial effect on the patient who was not suffering from neuropathy, but was suffering from pain. In all of the neuropathic patients, the effect lasted after the stimulation ceased. In all of the neuropathic patients, the effect lasted for a total of at least three hours, and in one of the patients the effect lasted for five days.

Seven of the neuropathic patients had been treated with a wide range of anti-neuropathic pain medications, without significant improvement in their pain. These patients stated that tibial nerve stimulation was the only procedure that substantially improved their symptoms. One of the neuropathic patients had not received any medications, and the stimulation was the first treatment of her neuropathic pain. This patient experienced marked improvement of pain in both sides, although the improvement was more pronounced in the stimulated side.

In about half of the neuropathic patients, the beneficial effect of the stimulation (i.e., the pain relief) was bilateral, despite the stimulation having been applied to the tibial nerve of one side only. The inventors hypothesize that this is due to a spinal cord loop.

Based on the results of the aforementioned experiment, in accordance with some applications, the following treatment is applied to a subject who is identified as suffering from polyneuropathy. Implantable element 10 (shown in FIG. 1) is implanted in contact with or in the vicinity of the subject's tibial nerve, for example, in accordance with the techniques described hereinabove. External controller 26 (also shown in FIG. 1), or an implantable controller that is generally similar to external controller 26 is used to drive the electrodes to drive a current into the tibial nerve for a therapy period. For example, the therapy period may last more than 30 minutes, and/or less than three hours. Alternatively, the therapy period may last more than two minutes, less than 10 minutes, and/or for a different period of time.

For some applications, therapy is administered to the subject once a day, several times (e.g., more than two, and/or less than eight times) a week or more, and/or in several therapy periods (e.g., more than two, and/or less than eight periods) over the course of a day. Typically, the length and/or frequency of the therapy periods is reduced, in response to the subject's condition improving. For some applications, therapy periods are applied on demand, based upon the subject feeling pain.

For some applications, the apparatus includes a lock-out mechanism to prevent the subject from applying the treatment for more than a maximal safe number of therapy periods over a given time period. During the therapy period the subject wears sock 28, or uses other means for keeping the external controller in the vicinity of the implantable element.

As described above, in about half of the neuropathic patients, the beneficial effect of the stimulation (i.e., the pain relief) was bilateral, despite the stimulation having been applied to the tibial nerve of one side only. Based on the results of the aforementioned experiment, in accordance with some applications, it is hypothesized that stimulation of a tibial nerve of a limb contralateral to that in which pain is experienced, may provide pain relief for subjects in whom such stimulation would not be desirable, justifiable, or even possible, in the limb that is ipsilateral to the pain being experienced. That is, in such subjects, pain may be treated by stimulating a contralateral limb. For example, the limb in which pain is being experienced (i.e., the ipsilateral limb) may have been damaged by disease (e.g., diabetes) or trauma, such that the ipsilateral limb is unsuitable to receive implanted apparatus. Similarly, in unilateral leg amputees who experience pain in the remaining leg, it may be undesirable to implant apparatus ipsilaterally. In such a case, stimulation may be applied to the contralateral leg (i.e., to the stump). Conversely, in unilateral amputees who experience phantom pains associated with the amputated limb, the ipsilateral tibial nerve in the stump may simply be absent or otherwise unavailable to be stimulated. In such a case, stimulation may be applied to the contralateral, remaining, leg. For each of these examples, it may be that little or no pain is experienced in the contralateral limb, and thus it would ordinarily be undesirable and/or unnecessary to implant tibial nerve stimulation apparatus in the contralateral limb. However, it is hereby hypothesized that such implantation may be beneficial to such subjects by providing bilateral pain relief, thereby providing pain relief in a limb that is generally less available for treatment by implantation of stimulation apparatus therein.

The implantation sites and disorders described hereinabove are examples for illustrating the use of the techniques described herein. The implants described herein may be implanted at a variety of implantation sites, and the techniques described herein may be used to treat a variety of disorders. For example:

stimulation of the tibial nerve (and/or of sensory fibers that lead to the tibial nerve), e.g., to treat neuropathic pain and/or urge incontinence;

stimulation of sensory fibers that lead to the radial and/or ulnar nerves, e.g., to treat tremor (e.g., essential tremor, and tremor associated with Parkinson's disease);

stimulation of the occipital nerve, e.g., to treat migraine;

stimulation of the sphenopalatine ganglion, e.g., to treat cluster headaches;

stimulation of the sacral and/or pudendal nerve, e.g., to treat urge incontinence;

direct stimulation of an implantation site within the brain (e.g., deep brain stimulation), such as the thalamus, e.g., to treat tremor, obsessive-compulsive disorder, and/or depression;

stimulation of the vagus nerve, e.g., to treat epilepsy, depression, inflammation, tinnitus, and/or congestive heart failure (e.g., by incorporating some or all of device 20 into an aortic stent);

stimulation of baroreceptors in a blood vessel wall (e.g., the wall of the carotid sinus and/or aorta, e.g., to treat high blood pressure;

stimulation of the spinal cord, e.g., to treat pain;

stimulation of one or more muscles (such as shoulder muscles), e.g., to treat muscle pain;

stimulation of the medial nerve, e.g., to treat carpal tunnel syndrome;

stimulation of the hypoglossal nerve and/or one or more muscles of the tongue, e.g., to treat obstructive sleep apnea;

stimulation of cardiac tissue, e.g., to pace and/or defibrillate the heart (e.g., the use of the implant as a leadless pacemaker);

stimulation to treat dystonia;

stimulation of the vagus nerve, e.g., to treat epilepsy;

stimulation to treat interstitial cystitis;

stimulation to treat gastroparesis;

stimulation to treat obesity;

stimulation of the anal sphincter, e.g., to treat fecal incontinence;

stimulation to treat bowel disorders;

stimulation of peripheral nerves of the spinal cord, e.g., to treat chronic pain;

stimulation of the dorsal root ganglion for the treatment of chronic pain; and stimulation of motor nerves and/or muscles to improve mobility.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
 identifying a subject as suffering from pain in a first limb of the subject; and
 in response to the identifying, treating the pain in the first limb by:
  implanting electrodes in a limb of the subject that is contralateral to the first limb, and
  inducing driving of the electrodes to apply a pain-relieving current to the contralateral limb.

2. The method according to claim 1, wherein identifying the subject as suffering from pain in the first limb, comprises identifying a subject as suffering from pain in a limb that has been damaged by trauma.

3. The method according to claim 1, wherein identifying the subject as suffering from pain in the first limb, comprises identifying a subject as suffering from phantom pain in a limb that has been amputated.

4. The method according to claim 1, wherein identifying the subject as suffering from pain in the first limb, comprises identifying a subject as suffering from pain in a limb that is contralateral to a limb that has been amputated, and wherein implanting electrodes in the contralateral limb comprises implanting electrodes in a stump of the limb that has been amputated.

5. The method according to claim 1, wherein identifying comprises identifying the subject as suffering from neuropathic pain in the first limb.

6. The method according to claim 1, wherein identifying the subject as suffering from pain in the first limb, comprises identifying a subject as suffering from pain in a limb that has been damaged by disease.

7. The method according to claim 6, wherein identifying the subject comprises identifying a subject as suffering from pain in a limb that has been damaged by diabetes.

8. The method according to claim 1, wherein inducing driving the electrodes comprises inducing driving the electrodes from outside a body of the subject.

9. The method according to claim 8, wherein inducing driving the electrodes from outside the body of the subject comprises inducing driving the electrodes using a control unit that is coupled to an element that is coupled to the contralateral limb.

10. The method according to claim 1, wherein inducing driving the electrodes to apply the current comprises inducing driving the electrodes to apply a current having a frequency of 10 Hz to 100 Hz.

11. The method according to claim 1, wherein inducing driving the electrodes to apply the current comprises inducing driving the electrodes to apply a current having a frequency of 20 Hz to 100 Hz.

12. The method according to claim 11, wherein inducing driving the electrodes to apply the current comprises inducing driving the electrodes to apply a current having a frequency of 20 Hz to 40 Hz.

13. The method according to claim 11, wherein inducing driving the electrodes to apply the current comprises inducing driving the electrodes to apply a current having a frequency of 40 Hz to 60 Hz.

14. The method according to claim 1, wherein inducing driving the electrodes to apply the current comprises inducing driving the electrodes to apply the current for a therapy period having a duration of between two minutes and ten minutes.

15. The method according to claim 14, wherein inducing driving the electrodes to apply the current for the therapy period comprises inducing driving the electrodes to apply the current during 2-8 therapy periods per day.

16. The method according to claim 14, wherein inducing driving the electrodes to apply the current for the therapy period comprises inducing driving the electrodes to apply the current during 2-8 therapy periods per week.

17. The method according to claim 1, wherein inducing driving the electrodes to apply the current comprises inducing driving the electrodes to apply a current having an amplitude of up to 10 mA.

18. The method according to claim 17, wherein inducing driving the electrodes to apply the current comprises inducing driving the electrodes to apply a current having an amplitude of between 0.2 mA and 8 mA.

19. The method according to claim 18, wherein inducing driving the electrodes to apply the current comprises inducing driving the electrodes to apply a current having an amplitude of between 0.5 mA and 4 mA.

20. The method according to claim 1, further comprising detecting a myographic signal of the subject, wherein inducing driving the electrodes comprises inducing driving the electrodes responsively to the myographic signal.

21. The method according to claim 1, wherein implanting the electrodes in the contralateral limb comprises placing the electrodes within 1 mm of a tibial nerve of the contralateral limb.

22. The method according to claim 21, wherein placing the electrodes comprises placing the electrodes within 0.5 mm of the tibial nerve of the contralateral limb.

23. The method according to claim 22, wherein placing the electrodes comprises placing the electrodes within 0.3 mm of the tibial nerve of the contralateral limb.

24. The method according to claim 23, wherein placing the electrodes comprises placing the electrodes in contact with the tibial nerve of the contralateral limb.

25. The method according to claim 24, wherein placing the electrodes comprises inserting the electrodes into the tibial nerve.

26. The method according to claim 25, wherein inserting the electrodes into the tibial nerve comprises expanding a spring, the electrodes being coupled to the spring.

27. The method according to claim 1, wherein the electrodes are disposed on a housing, and wherein implanting the electrodes comprises implanting the housing on which the electrodes are disposed.

28. The method according to claim 27, wherein implanting the electrodes comprises placing the electrodes within 1 mm of the tibial nerve, between the nerve and the housing, such that when the electrodes are driven to drive the current into the tibial nerve, the housing reduces a current path from the electrodes away from the tibial nerve.

29. The method according to claim 27, wherein implanting the housing comprises implanting a housing that is at least partially flexible.

30. The method according to claim 29, wherein the housing includes flexible and rigid portions thereof, the portions being articulatably coupled to each other, and wherein implanting the electrodes comprises implanting the housing that includes the flexible and the rigid portions thereof.

31. The method according to claim 27, wherein implanting the electrodes comprises placing the electrodes within 1 mm of a tibial nerve of the contralateral limb.

32. The method according to claim 31, wherein placing the electrodes within 1 mm of the tibial nerve of the subject comprises injecting the housing into an ankle of the subject.

33. The method according to claim 31, wherein placing the electrodes within 1 mm of the tibial nerve of the subject comprises coupling the housing to the tibial nerve via one or more coupling elements that are coupled to the housing.

34. The method according to claim 33, wherein coupling the housing to the tibial nerve via the one or more coupling elements comprises coupling the housing to the tibial nerve via one or more spiral coupling elements.

35. The method according to claim 31, wherein placing the electrodes within 1 mm of the tibial nerve of the subject comprises inserting the electrodes into the tibial nerve.

36. The method according to claim 35, wherein inserting the electrodes into the tibial nerve comprises positioning the electrodes adjacent to the tibial nerve by moving the housing alongside the tibial nerve in a first direction, and, subsequently, inserting the electrodes into the tibial nerve by moving the housing in a second direction, the second direction being opposite to the first direction.

* * * * *